United States Patent [19]
Catipovic et al.

[11] Patent Number: 5,320,596
[45] Date of Patent: Jun. 14, 1994

[54] CERVICAL ORTHOSIS

[75] Inventors: Robert M. Catipovic, Grand Island; Joseph C. Mollendorf, Amherst; Lilian A. Pascale, Niagara Falls, all of N.Y.

[73] Assignee: The Research Foundation of State Univ. of NY, Albany, N.Y.

[21] Appl. No.: 990,160

[22] Filed: Dec. 14, 1992

[51] Int. Cl.$^5$ .............................................. A61F 5/04
[52] U.S. Cl. ............................ 602/18; 128/DIG. 23; 602/6
[58] Field of Search ................. 602/5, 6, 8, 17–19; 128/DIG. 23

[56] References Cited

U.S. PATENT DOCUMENTS

| | | | |
|---|---|---|---|
| 443,764 | 12/1890 | Hilliard | 602/19 |
| 1,301,276 | 4/1919 | Kroetz | |
| 2,735,424 | 2/1956 | Benjamin | |
| 3,667,457 | 6/1972 | Zumaglini | 602/19 |
| 3,724,452 | 4/1973 | Nitschke | 602/18 |
| 3,756,226 | 9/1973 | Calabrese et al. | |
| 4,502,471 | 3/1985 | Owens | |
| 4,732,144 | 3/1988 | Cunahan | 602/18 |
| 5,003,968 | 4/1991 | Mars | 602/17 |
| 5,038,759 | 8/1991 | Morgenstern | |

*Primary Examiner*—Richard J. Apley
*Assistant Examiner*—Linda C. M. Dvorak
*Attorney, Agent, or Firm*—Ronald T. Coslick, Jr.

[57] ABSTRACT

A cervical orthosis is provided which supports the weight of the head with a chin support having a pair of transverse members extending rearward from the chin support to the wearer's shoulder. The transverse members are joined at the shoulder to a pair of vertical members which travel down the wearer's back. The orthosis is secured to the wearer by means of a belt attached to the lower ends of the transverse member which is fastened about the wearer's torso. In a preferred embodiment the orthosis is formed of one continuous piece of a suitably rigid material and conforms to the contours of the wearer's body. A method of forming a customized orthosis to conform to the contours of a wearer positioned in a desired posture is also provided.

12 Claims, 8 Drawing Sheets

CERVICAL ORTHOSIS

This invention was made with government support under Grant No. BCS 8908104 awarded by the National Science Foundation. The government has certain rights in this invention.

BACKGROUND OF THE INVENTION

This invention relates to cervical orthopedic devices. More particularly, the invention relates to rigid devices for supporting the weight of the head through application of a supporting force by a supporting member in contact with the underside of the chin, and to devices for the control of cervical flexion, cervical extension, and cervical rotation, as well as kyphotic back.

It is sometimes necessary to restrict the range of motion of a patient's head, or to support the weight of a patient's head using orthotic means. This is typically accomplished by encircling the neck with a semi-rigid collar which supports the head while restricting or preventing cervical flexion, extension, and rotation. When securely fixed about the neck, such collars form chin supporting surface beneath the chin upon which the weight of the head is rested. Such a device is disclosed, for example, in U.S. Pat. No. 3,756,226 to Calabrese, and U.S. Pat. No. 5,038,759 to Morgenstern. It is sometimes necessary to use the collar in combination with a larger stabilizing device which is fastened about the chest and to which the collar is fixed to form a load-bearing member between the collar and the chest. Such a device is disclosed, for example, in U.S. Pat. No. 4,502,471 to Owens.

Cervical collars have inherent disadvantages to the wearer. Collars generally have a large surface area in contact with the skin, resulting in the undesirable trapping of perspiration and retention of body heat which cause discomfort to the wearers. Collars are also bulky and cannot be worn beneath clothing. In addition, cervical collars are typically constructed of semi-rigid materials which are not sufficiently resilient to retain their shape for more than several days of continuous use, and often are not stiff enough to provide full support even in the course of normal use.

Stabilizers, which are designed to transfer the entire weight of the head directly from the chin through the collar to the chest, may be awkward and uncomfortable for some wearers because they impinge directly on the wearer's chest. In addition, stabilizers may not fit or stabilize other patients with certain physical characteristics such as kyphosis.

Additionally, collars by their design are effective only as barriers to cervical flexion and extension. Consequently, they are inadequate for providing proper positioning of the head for wearers whose problems result from improper positioning of the thoracic spine. For example, a cervical collar is not effective to provide proper positioning for a wheelchair-bound patient who tends to slump forward in his chair. In a similar sense, collars are unable to compensate for other abnormal forward curvature of the upper spine such as kyphosis.

It is therefore the object of this invention to provide a cervical orthosis which avoids use of the chest as a load bearing surface, which improves wearer comfort through minimization of surface area of the device in contact with the skin, which may be worn beneath clothing with minimal cosmetic effects to the wearer, which avoids the creation of uncomfortable load bearing pressure points, and which further may be employed to control the position of the head when such requires a repositioning of the forward curvature of the thoracic spine. It is a further object of this invention to provide a cervical orthosis which will function effectively irrespective of the presence of kyphosis.

SUMMARY OF THE INVENTION

The present invention is a rigid cervical orthosis which distributes the force from the weight of the head to the shoulders and the lower anterior torso through lever action pivoted at the shoulder. The device is preferably constructed of a moldable material formed into one piece which has a chin support having a pair of rigid transverse members extending rearward along the wearer's lower jaw and neck to the shoulder. The transverse members join vertical members at the shoulder which extend for a predetermined distance down the length of the back. At the lower ends of the vertical members a belt means is provided to be fastened around the wearer's torso. In this manner downward force from the weight of the head is rested on the chin support, pivoted about the shoulders, and ultimately transferred to the lower anterior torso by the inward pull of the belt means. An additional element may be added to the orthosis to limit cervical extension. The device may be produced in standard sizes, which may be worn as fabricated or may be subsequently custom fitted to the individual wearer. The device may also be created from a mold of the patient's body such that a custom made orthosis is provided. For patients with sufficient flexibility, the orthosis may be further designed to correct for kyphosis by molding the orthosis such that when in use it will reposition the thoracic spine to cause the wearer to conform to a desired posture. Alternatively, the orthosis may be designed to conform to such curvature while maintaining its effectiveness in supporting the head.

BRIEF DESCRIPTION OF THE DRAWINGS

For the purpose of illustrating the invention, there are shown in the drawings several possible embodiments of the invention including a preferred embodiment; however, the invention is not limited to the precise embodiments shown.

DETAILED DESCRIPTION OF PREFERRED EMBODIMENT

Figure 1:
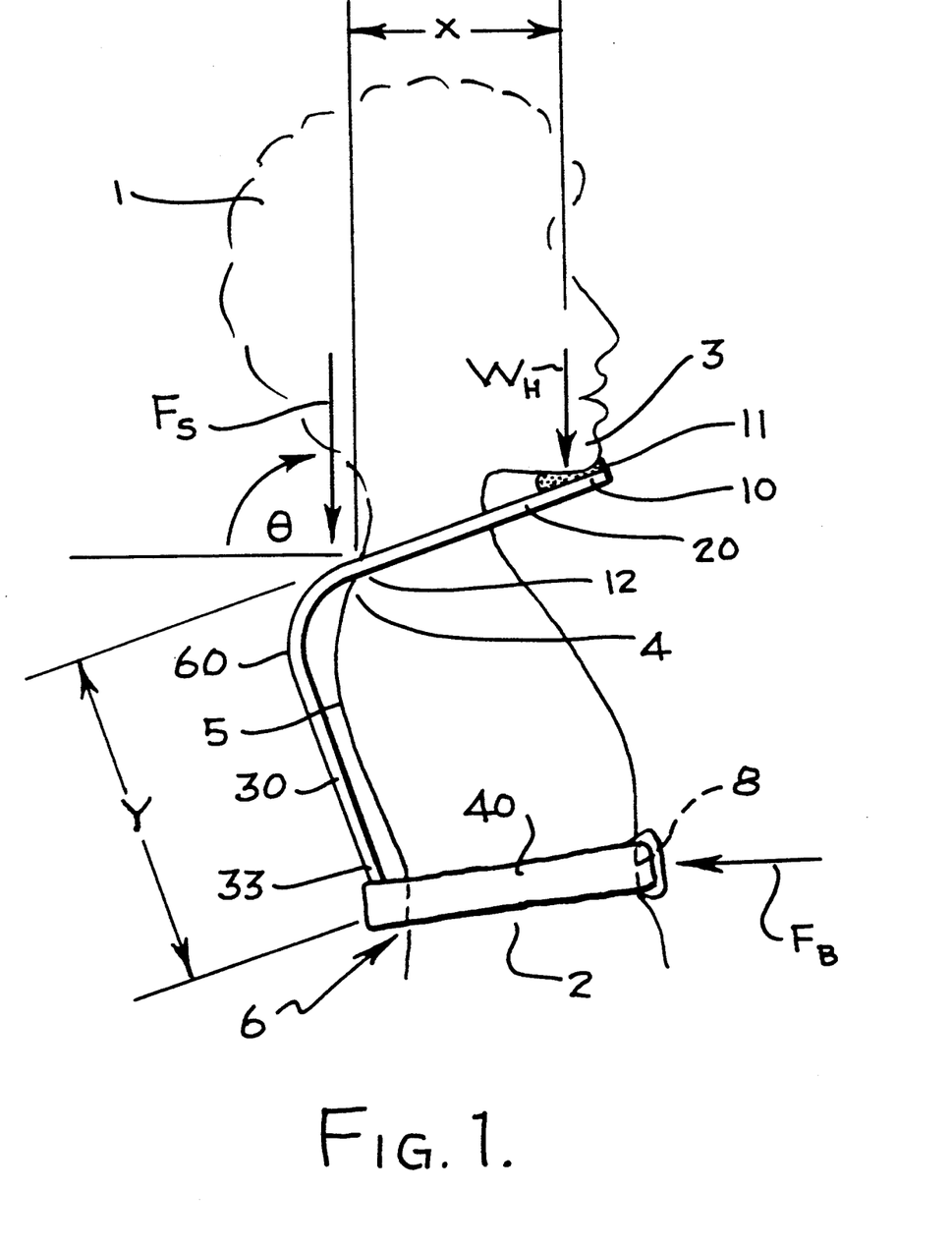
FIG. 1 is a free body diagram showing the forces resulting from the weight of the head which are transmitted to the body of an individual wearing the disclosed orthosis.

Referring to the drawings in detail, FIG. 1 shows the forces $F_s$ and $F_B$ born at the wearer's shoulder 4 and lower anterior torso 2, respectively, which result from support of the weight $W_H$ of the head 1 by the cervical orthosis 60. The weight $W_H$ of the head 1 is born at a chin supporting surface 11 on a chin support 10 from which extends a transverse member 20. The transverse member 20 has a horizontal length X which is approximately equal to the fixed distance between the wearer's chin 3 and the pivot point 12 near the top of the wearer's shoulder 4. The transverse member 20 is joined to a vertical member 30 of vertical length Y which extends down the wearer's back 5 from the transverse member at the pivot point 12. The wearer will bear a force $F_s$ at the pivot point 12 as a result of the weight of the head 1 being pivoted about the shoulder 4. The vertical member at its lower end 33 is provided with a belt means 40 which transfers a resultant force $F_B$ to the wearer's lower anterior torso 2 at a belt contact area 8, which lies between the wearer's ribs and waist line.

The relative lengths of the transverse and vertical members are determinative of the forces born by the body at both the pivot point at the shoulder and at the wearer's lower anterior torso. In designing an orthosis for a particular patient, the length of the transverse member will be a fixed distance, and therefore the length of the vertical member will determine the relative magnitudes of forces $F_S$ and $F_B$. The angle of the force born by the shoulder is represented as $\Theta$ in FIG. 1.

Summing the forces, it is found that $F_B = W_H/\sin\Theta$, $F_B = W_H/\tan\Theta$, and $Y/X = \tan\Theta$. It is desirable to minimize both $F_S$ and $F_B$; however, it is also necessary that length Y not be so great as to constrain movement in the area 6 of the lumbar vertebra. In addition, since human skin cannot comfortably bear continuous pressures greater than about 3 psi and may suffer breakdown at higher pressures, the minimum contact areas necessary to comfortably distribute the forces at the wearer's chin, shoulder and lower anterior torso are an equally important consideration. It is of course desirable to minimize those areas of contact by minimizing the forces born at those areas. Assuming $W_H = 15$ lbs and a maximum bearable pressure of 3 psi, and treating X as a fixed distance, it is shown in Table 1 that an optimal balance of the several foregoing considerations is achieved where $\Theta$ is approximately 60 degrees, and length Y is approximately 1.7 times length X. Using the above equations, it can be seen that $\Theta$ and length Y may be varied to provide optimal fit and comfort to the individual wearer.

TABLE 1

| Angle of Impingement of $F_S$ and Resulting Forces and Minimum Areas of Contact at Each Surface | | | | |
|---|---|---|---|---|
| $\Theta$ | $F_S$ in lbf | $F_B$ in lbf | Y/X | $A_S$ in in$^2$ | $A_B$ in in$^2$ |
| 30 | 30.0 | 26.0 | 0.6 | 10.0 | 8.7 |
| 45 | 21.2 | 15.0 | 1.0 | 7.1 | 5.0 |
| 50 | 19.6 | 12.6 | 1.2 | 6.5 | 4.2 |
| 55 | 18.3 | 10.5 | 1.4 | 6.1 | 3.5 |
| 58 | 17.7 | 9.4 | 1.6 | 5.9 | 3.1 |
| 59 | 17.5 | 9.0 | 1.7 | 5.8 | 3.0 |
| 60 | 17.3 | 8.7 | 1.7 | 5.8 | 2.9 |

TABLE 1-continued

| Angle of Impingement of $F_S$ and Resulting Forces and Minimum Areas of Contact at Each Surface | | | | |
|---|---|---|---|---|
| $\Theta$ | $F_S$ in lbf | $F_B$ in lbf | Y/X | $A_S$ in in$^2$ | $A_B$ in in$^2$ |
| 61 | 17.2 | 8.3 | 1.8 | 5.7 | 2.8 |
| 62 | 17.0 | 8.0 | 1.9 | 5.7 | 2.7 |
| 65 | 16.6 | 7.0 | 2.2 | 5.5 | 2.3 |
| 70 | 16.0 | 5.5 | 2.8 | 5.3 | 1.8 |

Figure 2:
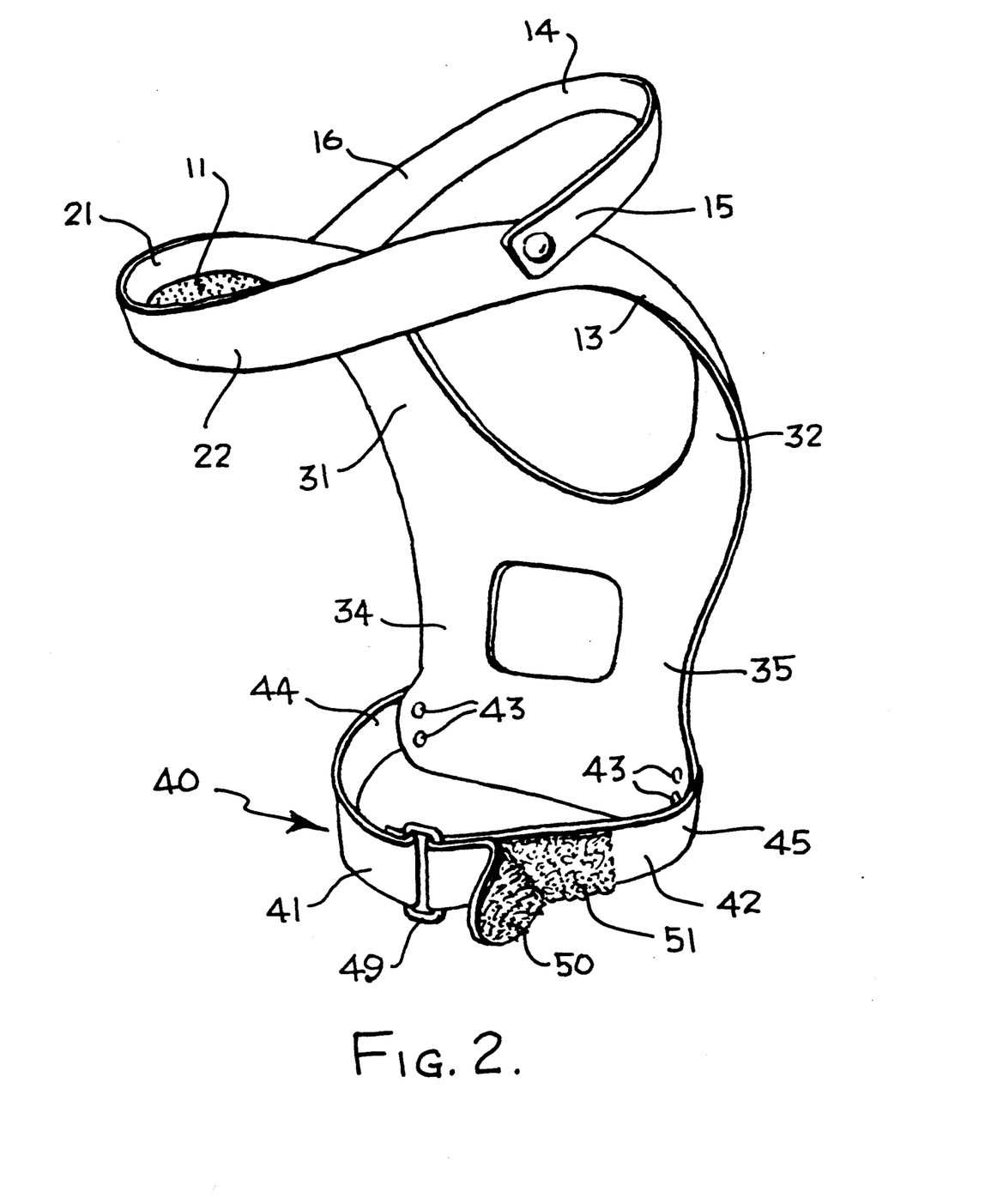
FIG. 2 is a perspective view of the embodiment of FIG. 5 which includes a belt with a VELCRO fastening apparatus shown in a partially unfastened configuration.
Figure 3:
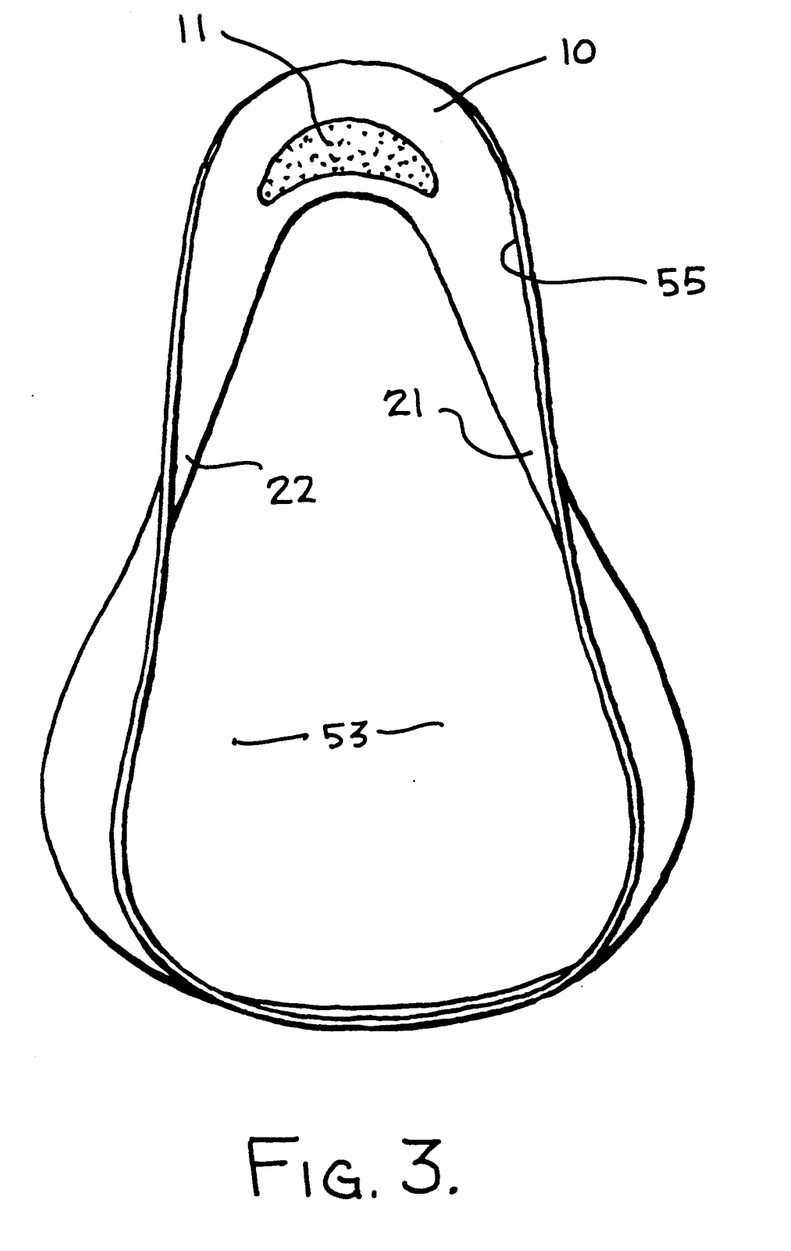
FIG. 3 is an overhead view of the device showing the chin support surface.

FIGS. 2 and 3 illustrate a preferred embodiment of the invention, in which a chin support 10 is provided which has a chin supporting surface 11. The chin supporting surface is shaped to conform generally to the shape of the underside of the wearer's chin, and the chin support is cupped to keep the chin seated on the chin supporting surface, thereby preventing cervical rotation when the orthosis is in place. A pair of rigid transverse members 21 and 22 extends rearward from the chin support. For aesthetic purposes, the transverse members are preferably as narrow and thin as the material they are constructed of will allow. FIG. 2 shows a pair of transverse members which are thin and flat. The members begin at the chin support and extend rearward along the length of the lower jaw and beyond the neck to the shoulders, with their broader surfaces formed such that they conform generally to the contours of the wearer's lower jaw, neck, and shoulders.

At a point along the length of the transverse members 31 and 32, a cervical extension control means 14 is provided. The control means is fixed at its ends 15 and 16 to the transverse members 31 and 32. When in use, the control means extends about the back of the wearer's head, thereby limiting the wearer's degree of cervical extension. The control means 14 may be of a flexible, semirigid, or rigid material, and is detachably affixed to the transverse members 31 and 32 by any of several well known devices such as snaps or the like.

At the wearer's shoulders the transverse members 21 and 22 are joined to vertical members 31 and 32 which extend downward along the length of the wearer's back. At the lower ends 34 and 35 of the vertical members a belt means 40 is provided which is of sufficient length to be fastenable about the wearer's torso. The belt means may be of a rigid, semirigid, or flexible material. In the preferred embodiment, the belt means comprises a pair of joinable nylon belt segments 41 and 42 fixed to lower ends 34 and 35 respectively. The belt segments are fastened at their terminal ends 44 and 45 to the lower ends of the vertical members by rivets 43 or other secure fastening means. Other equivalent belt means such as a belt comprising a single continuous piece may be similarly employed. Such means are illustrated in FIG. 6.

Belt segments 41 and 42 are joinable at their joinable ends 46 and 47 by a secure fastening means 48 in which one belt segment 41 terminates in a metal ring 49, and the opposing belt segment 42 is provided with mating VELCRO fastening apparatus pieces 50 and 51 such that it may be passed through the metal ring and folded back upon itself and thereby secured. Other secure fastening means such as buckles, snaps, buttons or hooks may be similarly employed. Once the belt is fastened, the orthosis is secured on the wearer, and the belt provides for static distribution of the load produced by the weight of the head between the shoulder and lower anterior torso.

Figure 4:
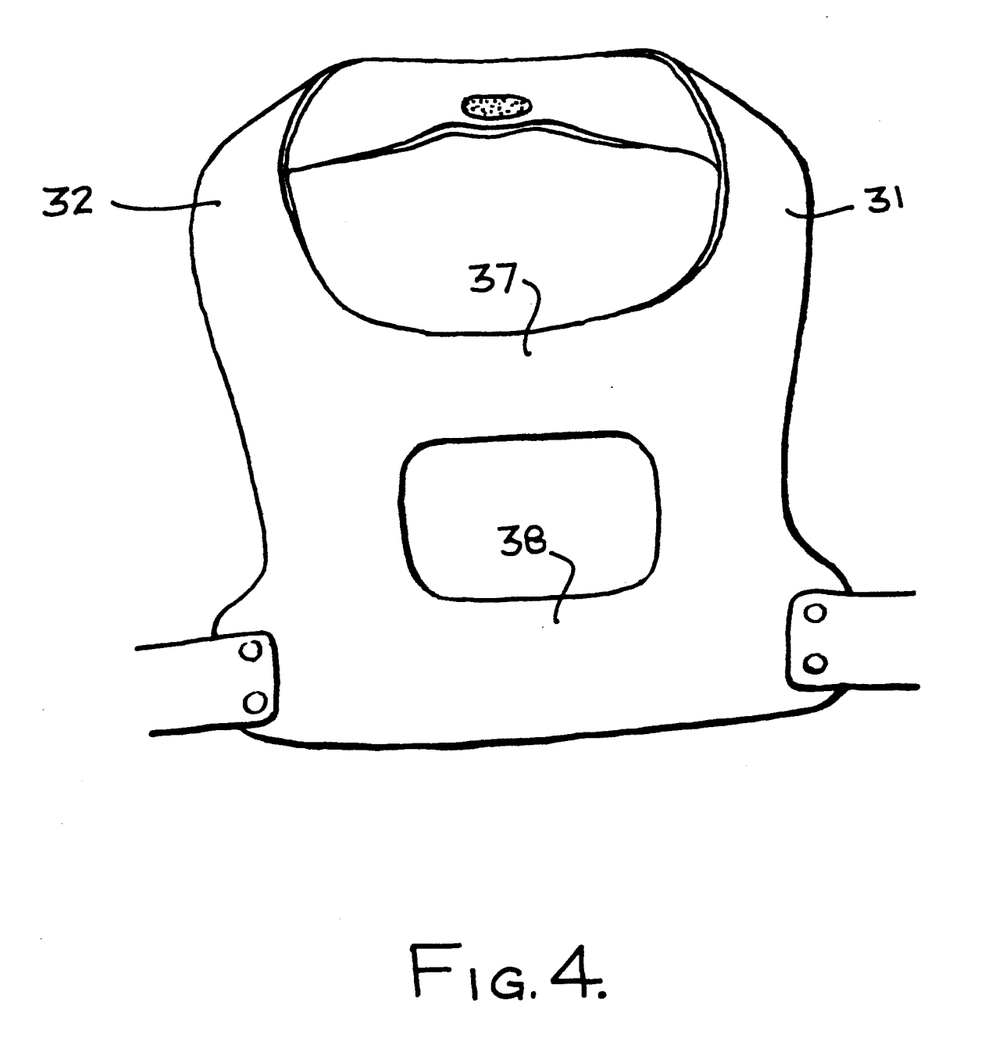
FIG. 4 is a rear view of an embodiment of the invention having two vertical members joined by a pair of joining members.
Figure 5:
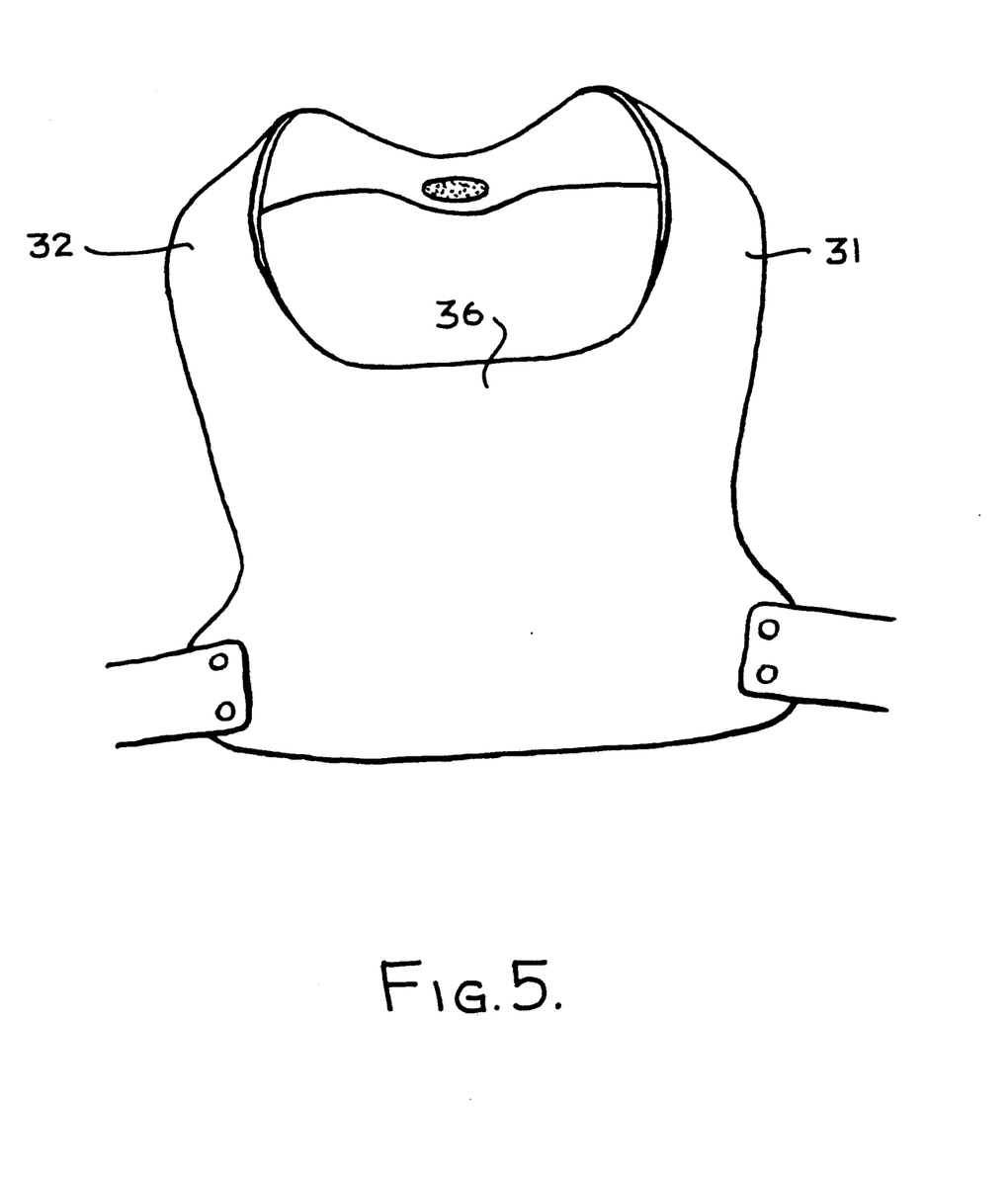
FIG. 5 is a rear view of an embodiment of the invention having two vertical members joined by a single broad joining member.
Figure 6:
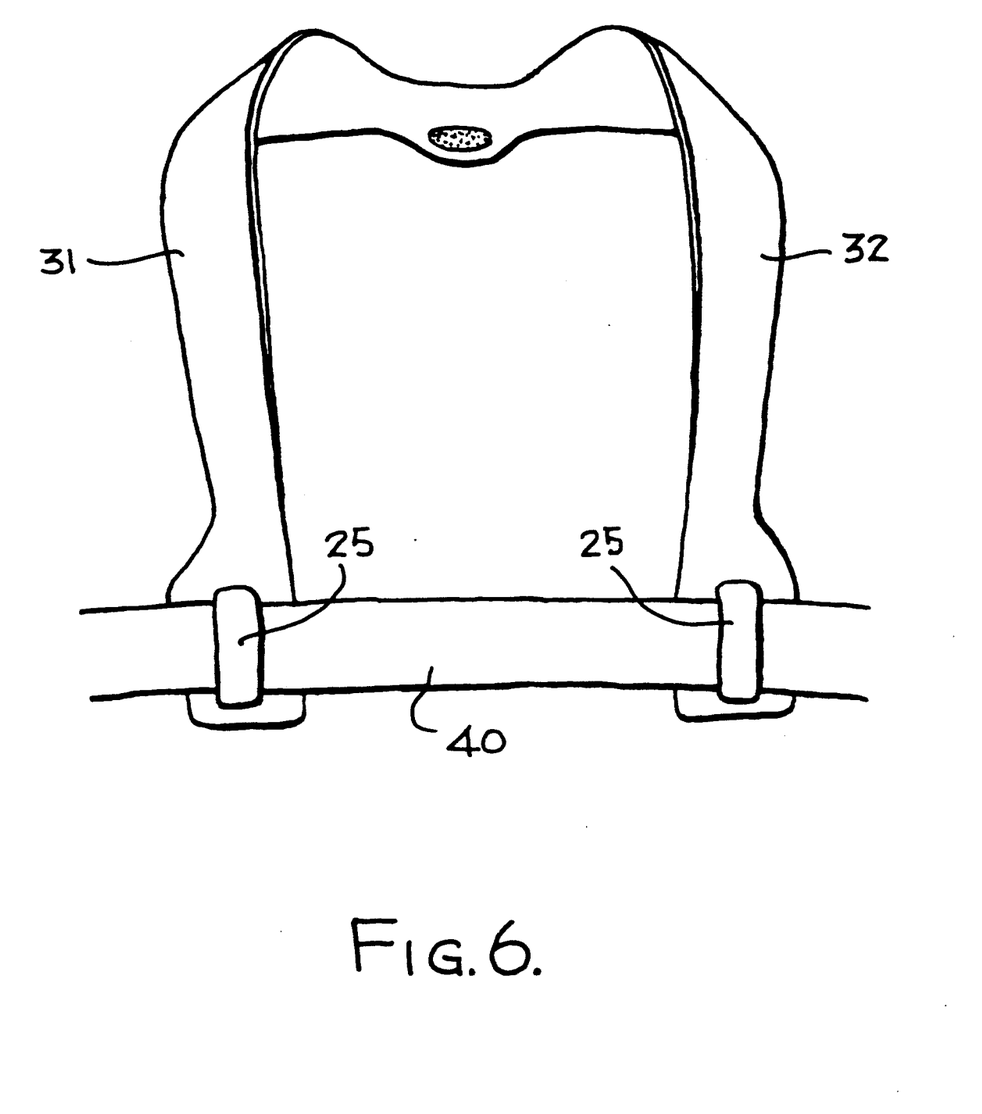
FIG. 6 is a rear view of an embodiment of the invention having a pair of vertical members and a single continuous belt means.
Figure 7:
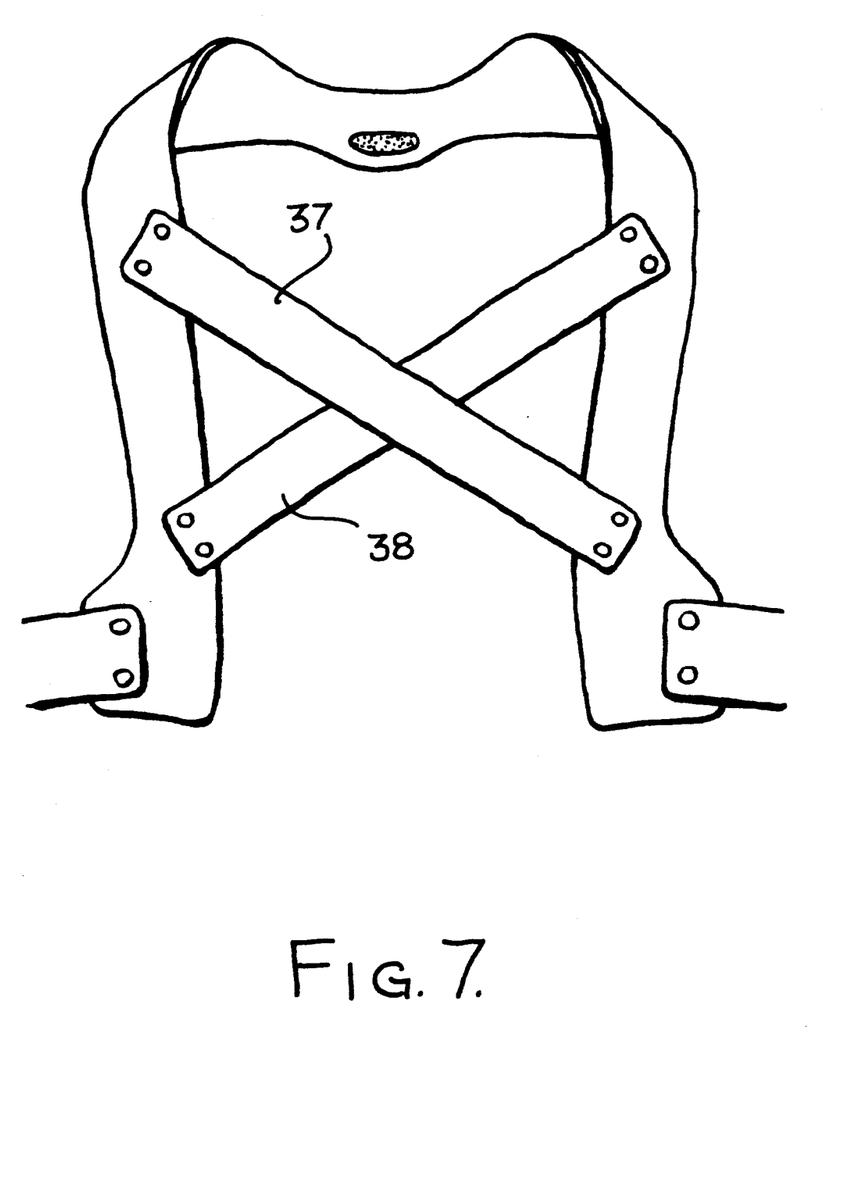
FIG. 7 is a rear view of an embodiment of the invention having a pair of vertical members joined by two flexible joining members.
Figure 8:
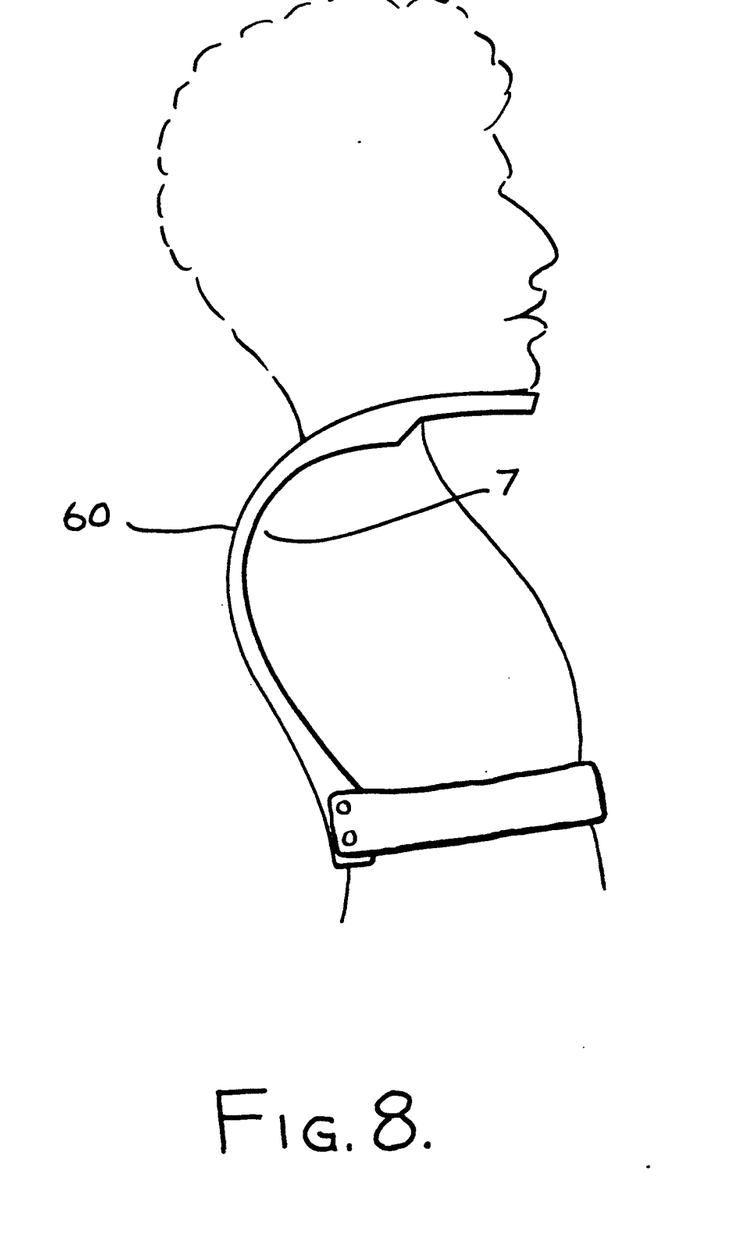
FIG. 8 shows an orthosis designed to conform to the features of a patient with an abnormal forward curvature of the upper spine.

The vertical members 31 and 32 which extend down the back may be unconnected, as illustrated in FIG. 6, or may be joined at a point below the shoulder by a joining member 36, as illustrated in FIG. 5. A plurality of smaller joining members 37 and 38 may be employed to reduce skin contact and thereby improve wearer comfort, as in the preferred embodiment shown in FIG. 4. The vertical and joining members, like the transverse members, are preferably as narrow and thin as possible to reduce weight and material costs. FIG. 4 shows joining members which are thin and flat, with their broad surfaces generally conforming to the contours of the wearer's body. The joining members are employed to prevent undesirable spreading of the vertical members due to tightening of the belt, and may be formed of the same rigid material as the transverse and vertical members, as illustrated in FIG. 4, or of some other material of suitable strength and elasticity. FIG. 7 illustrates an equivalent embodiment in which the joining members are of a suitable flexible material.

In the preferred embodiment as illustrated in FIGS. 2, 3, and 4, the chin support, a pair of transverse members, and a pair of vertical members are formed of one continuous piece of a suitably rigid material such as acrylic resin. A reinforcing compound such as graphite may be incorporated, as is well known in the art, to add strength to the chosen material where needed. Material strength is most crucial in the vicinity of the pivot point 12 at the wearer's shoulder When the orthosis is formed of a single continuous piece, it is essential that an opening is provided between the transverse members at the shoulder area which is sufficient to allow insertion of the wearer's head through the space and into proper position. FIG. 3 shows a keyhole-like space 53 which is large enough to allow passage of the wearer's head.

When in use the orthosis is in contact with the wearer's skin in several areas, most notably the belt contact area 8 shown in FIG. 1, the chin supporting surface 11 shown in FIG. 3, and the shoulder pivot surface 13 shown in FIG. 2. The orthosis should be designed so the wearer is not subjected to an uncomfortable amount of pressure at any of these points. Table 1 provides minimum contact surface areas $A_B$ and $A_S$ for various configurations of the orthosis. In the preferred embodiment as shown in FIG. 3, a thin lining 55 of a semi-rigid material such as foam rubber is provided between the orthosis and the skin to equalize the distribution of pressure over the areas of contact.

The orthosis may be produced in predetermined sizes through any well known technique such as injection molding. Custom made devices may also be produced by forming the orthosis directly on a model of the wearer. The following description is provided as one example of such a customizing process: A cotton stockinette is placed over the wearer to cover the area of the patient between the nose and waist. The wearer is then positioned in a posture to which the model and the orthosis are desired to conform. Plaster bandage splints are placed about the wearer so that an impression is made of the wearer in the areas to which the orthosis is intended to conform. The impression is allowed to harden and is then removed from the wearer and filled with plaster to create a model of the wearer. The model is smoothed and sealed with a parting lacquer. To form the orthosis, the model is covered with a polyvinyl-alcohol bag. This is covered with ½ oz. dacron felt, and then with 12 layers of 623T3 nylon alternated with carbon graphite matting. A second PVA bag is placed over the layup, which is then impregnated with carbonacrylic resin. After the resin has cured, trim lines are determined and the orthosis is removed from the model by breaking apart the model. The orthosis may be subsequently trimmed to the exact desired specifications, and the padding and belt means added. In this manner a rigid orthosis may be produced which functions effectively while conforming to the physical contours of the individual. As illustrated in FIG. 7, an orthosis 60 may be produced which conforms to the features of a wearer with a kyphotic back 7.

This customizing technique is especially useful in designing an orthosis which will correct both exaggerated cervical flexion and thoracic kyphosis in wearers who exhibit sufficient spinal flexibility. These may include patients with kyphosis or patients who are wheelchair bound and tend to slump forward. Since the orthosis is rigid, the wearer's spine will flex to conform to the contours of the orthosis when it is in place on the wearer. Consequently, a device may be produced using the above modeling technique where the initial cast is taken of the wearer while he is positioned in a posture to which he intends the orthosis to cause him to conform. An individual wearing such an orthosis will assume the same posture as that of the model from which the orthosis was cast.

What is claimed is:

1. A cervical orthosis comprising:
   a chin support having a chin supporting surface;
   at least one rigid transverse member extending rearward from said chin support, and being adapted to reach to and make contact with the wearer's shoulder;
   at least one rigid vertical member extending downward from the rearward end of said transverse member; and
   belt means, capable of being securely fastened about the torso of the wearer, disposed at the lower end of said vertical member;
   whereby a normal force at said chin supporting surface is distributed as normal forces at the wearer's shoulder and anterior torso.

2. The device according to claim 1 comprising a pair of transverse members extending rearward from said chin support and adapted to extend along opposite sides of the wearer's lower jaw.

3. The device according to claim 2 comprising a pair of vertical members, each of said vertical members extending downward from a separate and distinct transverse member.

4. The device according to claim 3 wherein the ratio of the lengths of the vertical members to those of the transverse members is in the range of 1.6 to 2.0.

5. The device according to claim 3 wherein the chin support, transverse member, and vertical member are formed of one continuous piece of a rigid material.

6. The device according to claim 5 further comprising at least one joining member disposed between and connecting said vertical members.

7. The device according to claim 5 further comprising cervical extension control means affixed to said transverse members.

8. The device according to claim 5 wherein a reinforcing material is employed within said rigid material in at least the region adjacent to the wearer's shoulder.

9. The device according to claim 5 further comprising a layer of padding material affixed at least to the skin contacting regions of the orthosis.

10. The device according to claim 5 wherein the orthosis is shaped to conform roughly to the natural contours to the wearer's lower jaw, neck, and back.

11. The device according to claim 5 wherein the orthosis is shaped to conform roughly to the natural contours to a wearer whose back is positioned in a desired and predetermined posture.

12. The device according to claim 5 wherein the orthosis is formed by the process of injection molding.

* * * * *